United States Patent
Koo et al.

(10) Patent No.: US 9,365,561 B2
(45) Date of Patent: Jun. 14, 2016

(54) C5 BENZOTHIAZOLYL SULFONE COMPOUND, METHOD OF PREPARING PREPARING THE SAME, METHOD OF PREPARING POLYENE DIALDEHYDE COMPOUND USING THE SAME, AND METHOD OF SYNTHESIZING LYCOPENE USING THE SAME

(71) Applicant: MYONGJI UNIVERSITY INDUSTRY AND ACADEMIA COOPERATION FOUNDATION, Gyeonggi-do (KR)

(72) Inventors: Sangho Koo, Seoul (KR); Jung Ae Choi, Jeollanam-do (KR); Eun-Taek Oh, Jeollanam-do (KR)

(73) Assignee: MYONGJI UNIVERSITY INDUSTRY AND ACADEMIA COOPERATION FOUNDATION (KR)

( * ) Notice: Subject to any disclaimer, the term of this patent is extended or adjusted under 35 U.S.C. 154(b) by 0 days.

(21) Appl. No.: 14/751,294

(22) Filed: Jun. 26, 2015

(65) Prior Publication Data

US 2015/0376175 A1    Dec. 31, 2015

(30) Foreign Application Priority Data

Jun. 30, 2014   (KR) .................. 10-2014-0080647

(51) Int. Cl.
*C07D 417/12* (2006.01)
*C07C 1/32* (2006.01)
*C07C 45/60* (2006.01)
*C07D 301/03* (2006.01)
*C07D 277/74* (2006.01)

(52) U.S. Cl.
CPC .............. *C07D 417/12* (2013.01); *C07C 1/322* (2013.01); *C07C 1/323* (2013.01); *C07C 45/60* (2013.01); *C07D 277/74* (2013.01); *C07D 301/03* (2013.01)

(58) Field of Classification Search
USPC ........................................................ 548/166
See application file for complete search history.

(56) References Cited

PUBLICATIONS

The Longest Polyene; Muhammad Zeeshan et al; Org. Lett., 2012,14 (21), pp. 5496-5498 (1 page).
Korean application No. 10-2014-0080647; Jun. 30, 2014 (34 pages).
"Synthesis of Symmetrical Carotenoids by a Two-Fold Stille Reaction"; Org. Chem. Jul. 2002. vol. 67, No. 14, (pp. 5040-5043); 4 pages, Vaz et al., J. Org. Chem., 2002.
"Efficient Total Synthesis of Lycophyll"; Org. Process Res. Dev., Sep. 2005., vol. 6, (pp. 830-836); 7 pages, Jackson et al.

*Primary Examiner* — Laura L. Stockton
(74) *Attorney, Agent, or Firm* — Mark E. Bandy; Rankin, Hill & Clark LLP

(57) ABSTRACT

Disclosed are a novel C5 benzothiazolyl sulfone compound having an acetal protecting group, a method of preparing the same, and a method of efficiently preparing an apo-carotene dialdehyde compound having a polyene dialdehyde structure using the same. Also, a method of efficiently preparing lycopene by olefination (Julia-Kocienski) between the apo-carotene dialdehyde compound (C20 crocetin dialdehyde) and C10 benzothiazolyl geranyl sulfone is provided.

5 Claims, No Drawings

C5 BENZOTHIAZOLYL SULFONE COMPOUND, METHOD OF PREPARING PREPARING THE SAME, METHOD OF PREPARING POLYENE DIALDEHYDE COMPOUND USING THE SAME, AND METHOD OF SYNTHESIZING LYCOPENE USING THE SAME

BACKGROUND OF THE INVENTION

1. Field of the Invention

The present invention relates to a C5 benzothiazolyl sulfone compound, a method of preparing the same, a method of preparing a polyene dialdehyde compound using the same, and a method of synthesizing lycopene using the same. Particularly, the present invention relates to a C5 benzothiazolyl sulfone compound, a preparation method thereof, a method of efficiently preparing crocetin dialdehyde ($C_{20}H_{24}O_2$) having a polyene dialdehyde structure using the sulfone compound and C30 and C40 apo-carotene dialdehydes homologous thereto, and a method of synthesizing lycopene using the sulfone compound. More particularly, the present invention relates to a novel C5 benzothiazolyl sulfone compound having an acetal protecting group derived from neopentyl glycol, a preparation method thereof, a method of efficiently preparing crocetin dialdehyde and homologous C30 ($C_{30}H_{36}O_2$) and C40 ($C_{40}H_{48}O_2$) apo-carotene dialdehyde compounds using the sulfone compound, and a method synthesizing lycopene via a double-bond formation reaction using the sulfone compound.

2. Description of the Related Art

The present invention pertains to a C5 benzothiazolyl sulfone compound having an acetal protecting group, a method of preparing the same, a method of efficiently preparing C20 crocetin dialdehyde having a polyene dialdehyde structure using the same and C30 and C40 apo-carotene dialdehyde compounds homologous thereto, and a method of synthesizing lycopene using sulfone synthesis.

In regard thereto, the following method is known. Specifically, a C5 Wittig salt having an acetal protecting group derived from neopentyl glycol is prepared, and then subjected to a Wittig reaction with crocetin dialdehyde, yielding a polyene dialdehyde compound homologous thereto (Cited Reference). However, this case is problematic because the reaction has to be carried out for about 20 min at high temperature using microwaves, the Z-double bond configuration is mainly formed due to the use of the Wittig salt that is difficult to purify, and phosphine oxide that is difficult to remove is generated as a byproduct.

CITED REFERENCE

Zeeshan, M.; Sliwka, H.-R.; Partali, V.; Martinez, A. Org. Lett. 2012, 14, 5496-5498.

SUMMARY OF THE INVENTION

Accordingly, the present invention is intended to provide a novel C5 benzothiazolyl sulfone compound having an acetal protecting group derived from neopentyl glycol and a method of preparing the same. Also, the present invention is intended to provide a method of efficiently preparing homologous apo-carotene dialdehyde compounds by repetitively reacting the sulfone compound with polyene dialdehyde. Also, the present invention is intended to provide a method of efficiently preparing lycopene by subjecting crocetin dialdehyde to a double-bond formation reaction using benzothiazolyl geranyl sulfone.

The present invention provides a C5 benzothiazolyl sulfone compound represented by Chemical Formula 1 below.

[Chemical Formula 1]

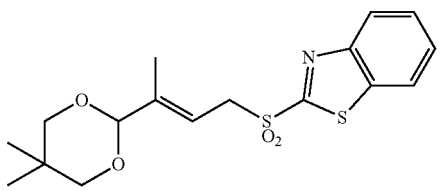

In addition, the present invention provides a method of preparing the C5 benzothiazolyl sulfone compound represented by Chemical Formula 1.

This method comprises: (a) oxidizing isoprene ($C_5H_8$), thus synthesizing isoprene monoxide represented by Chemical Formula 2 below; (b) subjecting isoprene monoxide to a ring opening reaction using 2-mercaptobenzothiazole, thus synthesizing hydroxyallylic benzothiazolyl sulfide represented by Chemical Formula 3 below; (c) oxidizing allylic alcohol contained in hydroxyallylic benzothiazolyl sulfide, thus synthesizing an unsaturated aldehyde containing benzothiazolyl sulfide represented by Chemical Formula 4 below; (d) subjecting the aldehyde to an acetal formation reaction using neopentyl glycol, thus synthesizing an acetal containing benzothiazolyl sulfide represented by Chemical Formula 5 below; and (e) oxidizing benzothiazolyl sulfide of the acetal, thus synthesizing C5 benzothiazolyl sulfone represented by Chemical Formula 1.

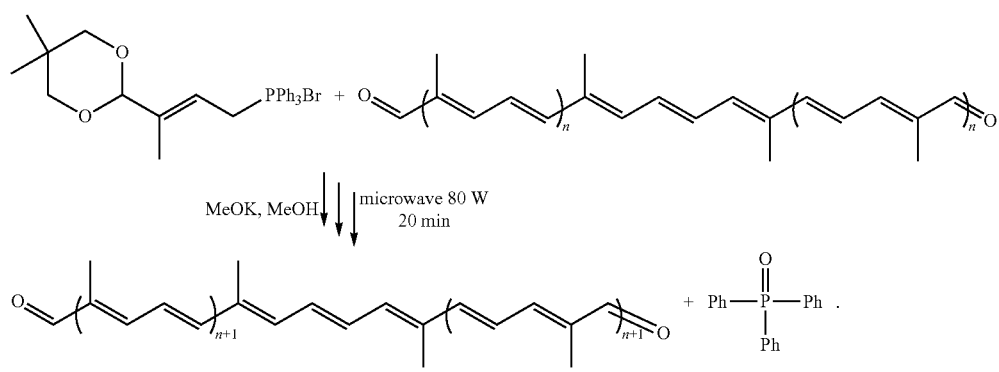

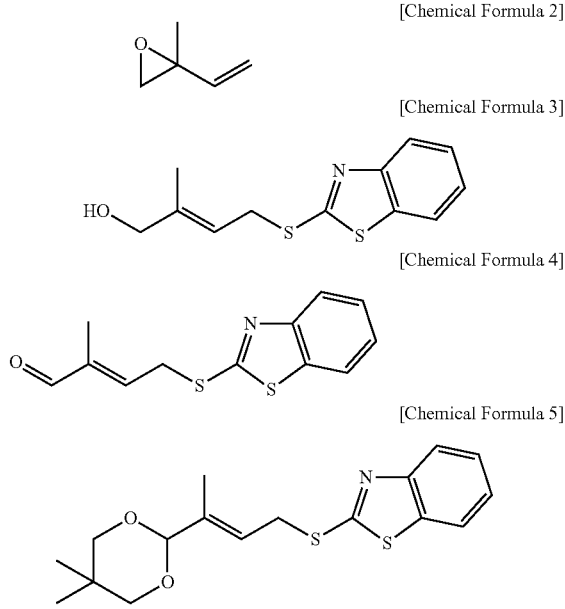

[Chemical Formula 2]

[Chemical Formula 3]

[Chemical Formula 4]

[Chemical Formula 5]

Specifically, oxidizing in (a) may be performed in a single step using isoprene and peroxycarboxylic acid but position selectivity of oxidation for isoprene is poor, and thus N-bromosuccinimide (NBS) may be reacted in water, thus position-selectively forming a bromohydrine compound, which is then reacted with an alkaline aqueous solution such as NaOH (Korean Patent No. 10-0398652).

The epoxide ring opening reaction in (b) may be performed by dissolving 2-mercaptobenzothiazole in a dimethylformamide (DMF) solvent and using a monovalent copper salt (CuCl, CuBr, CuI, or CuCN) as a catalyst (0.01~0.05 equivalents) (Korean Patent No. 10-0398652). As such, the sulfide represented by Chemical Formula 3 is selectively obtained, and E:Z selectivity of the double bond is 5:1 or higher.

Oxidizing the alcohol in (c) is performed in the absence of water, and PDC (pyridinium dichromate), PCC (pyridinium chlorochromate), $MnO_2$ or the like may be used by being dispersed in a $CH_2Cl_2$ solvent. To facilitate work-up of the reaction, silica gel may be added.

The acetal formation reaction in (d) may be performed using ethylene glycol, propylene glycol, and neopentyl glycol. Taking into consideration the stability of the compound, neopentyl glycol is preferably useful. The acetal formation reaction is implemented by adding p-TsOH in a catalytic amount (0.05 equivalents or less) in the presence of a benzene or toluene solvent and removing the produced water using a Dean-Stark column.

Selective oxidation of the sulfide into sulfone in (e) may be performed under known reaction conditions, including using hydrogen peroxide ($H_2O_2$) in the presence of any metal oxide catalyst, or using oxone, peroxycarboxylic acid, etc. Preferably, hydrogen peroxide is adsorbed to urea and then reacted with phthalic anhydride to give mono-perphthalic acid that is then reacted in the presence of an acetonitrile solvent.

These steps may further include dilution with an organic solvent, washing with water, drying over anhydrous $Na_2SO_4$, filtration, and concentration under reduced pressure.

Also, purifying using column chromatography may be further carried out.

The column chromatography may be silica gel flash column chromatography.

In addition, the present invention provides a method of preparing polyene dialdehyde represented by Chemical Formula 7 below, comprising: binding the C5 benzothiazolyl sulfone compound represented by Chemical Formula 1 with polyene dialdehyde represented by Chemical Formula 6 below at a molar ratio of 2:1, and then performing acid treatment, thus removing an acetal protecting group. The compound represented by Chemical Formula 7 is configured such that the compound represented by Chemical Formula 6 is extended by 10 carbon chains.

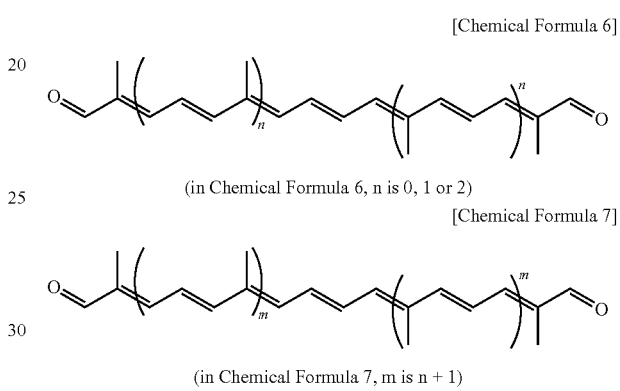

[Chemical Formula 6]

(in Chemical Formula 6, n is 0, 1 or 2)

[Chemical Formula 7]

(in Chemical Formula 7, m is n + 1)

The method of preparing polyene dialdehyde may include reacting the C5 benzothiazolyl sulfone compound represented by Chemical Formula 1 with C10 octatriene dialdehyde represented by Chemical Formula 6a below (in Chemical Formula 6, n=0) at a molar ratio of 2:1, and then performing acid treatment to remove an acetal protecting group, yielding C20 crocetin dialdehyde represented by Chemical Formula 7a below (in Chemical Formula 7, m=1).

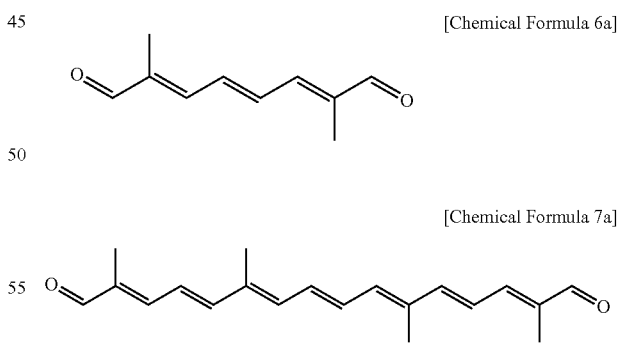

[Chemical Formula 6a]

[Chemical Formula 7a]

Binding benzothiazolyl sulfone represented by Chemical Formula 1 with C10 dialdehyde represented by Chemical Formula 6a, which is known as Julia-Kocienski olefination, is carried out at a low temperature of −78° C. for about 1~2 hr. During the binding reaction, Smiles rearrangement and removal of $SO_2$ and 2-hydroxybenzothiazole may occur simultaneously, thus directly forming a double bond (Baudin, J. B.; Hareau, G.; Julia, S. A.; Ruel, O. *Tetrahedron Lett.*

1991, 32, 1175-1178). The binding reaction is performed using a base such as NaHMDS, KHMDS, or LiHMDS in THF solvent and the use of metal ion such as Na or K is preferable in terms of forming a trans-double bond compared to the use of Li (Pospisil, J. *Tetrahedron Lett.* 2011, 52, 2348-2352).

Meanwhile, 2,7-dimethyl-2,4,6-octatrienedial represented by Chemical Formula 6a is a material widely used for synthesis of a carotene compound using a Wittig reaction, and preparation thereof is reported in many reports (*J. Org. Chem.* 1999, 64, 8051; WO 2000027810 A1; U.S. Pat. No. 5,471,005 A; DE 102004006579 A1).

The acetal protecting group formed from neopentyl glycol may be easily removed in the presence of a solvent mixture of a 1 M HCl aqueous solution and THF, and the addition of oxalic acid enables more efficient reaction.

The reaction between the C5 benzothiazolyl sulfone compound represented by Chemical Formula 1 and C10 octatriene dialdehyde represented by Chemical Formula 6a may be equally applied to homologous polyene dialdehyde compounds, thus providing polyene dialdehyde increased by 10 carbon atoms per reaction. This may be regarded as a general chain extension method for synthesis of apo-carotene dialdehyde.

Also, the method of preparing polyene dialdehyde may include reacting the C5 benzothiazolyl sulfone compound represented by Chemical Formula 1 with C20 crocetin dialdehyde represented by Chemical Formula 6b (in Chemical Formula 6, n=1) at a molar ratio of 2:1, and then performing acid treatment to remove an acetal protecting group, yielding C30 tetracosaundecaene dialdehyde represented by Chemical Formula 7b below (in Chemical Formula 7, m=2).

The acetal protecting group formed from neopentyl glycol may be easily removed in the presence of a solvent mixture of a 1 M HCl aqueous solution and THF, and the addition of oxalic acid enables more efficient reaction.

Also, the method of preparing polyene dialdehyde may include reacting the C5 benzothiazolyl sulfone compound represented by Chemical Formula 1 with C30 tetracosaundecaene dialdehyde represented by Chemical Formula 6c (in Chemical Formula 6, n=2) at a molar ratio of 2:1, and then performing acid treatment to remove two acetal protecting groups, yielding C40 dotriacontapentadecaene dialdehyde represented by Chemical Formula 7c below (in Chemical Formula 7, m=3).

[Chemical Formula 7c]

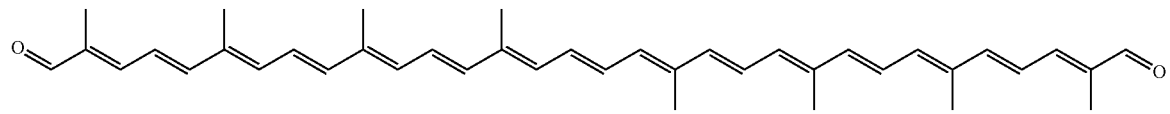

Binding benzothiazolyl sulfone represented by Chemical Formula 1 with C30 tetracosaundecaene dialdehyde represented by Chemical Formula 6c (in Chemical Formula 6, n=2) may be performed at a low temperature of −78° C. for about 1~2 hr, and Smiles rearrangement and removal of $SO_2$ and 2-hydroxybenzothiazole may take place simultaneously, thus directly forming a double bond. The binding reaction is performed using a base such as NaHMDS, KHMDS, or LiHMDS in the presence of THF solvent, and the use of metal ion such as Na or K is preferable in terms of forming a trans-double bond compared to the use of Li.

The acetal protecting group formed from neopentyl glycol may be easily removed in the presence of a solvent mixture of a 1 M HCl aqueous solution and THF, and the addition of oxalic acid enables more efficient reaction.

Finally, the present invention provides a method of preparing lycopene represented by Chemical Formula 9 below, comprising reacting C20 crocetin dialdehyde represented by

[Chemical Formula 7b]

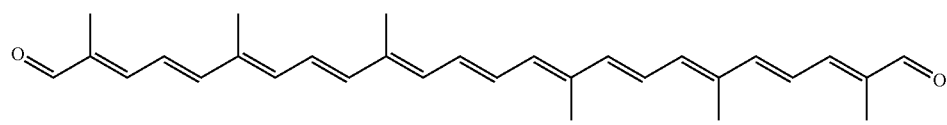

Binding benzothiazolyl sulfone represented by Chemical Formula 1 with C20 crocetin dialdehyde represented by Chemical Formula 6b (in Chemical Formula 6, n=1) may be performed at a low temperature of −78° C. for about 1~2 hr, and Smiles rearrangement and removal of $SO_2$ and 2-hydroxybenzothiazole may occur simultaneously, thus directly forming a double bond. The binding reaction is conducted using a base such as NaHMDS, KHMDS, or LiHMDS in the presence of THF solvent, and the use of metal ion such as Na or K is preferable in terms of forming a trans-double bond compared to the use of Li.

Chemical Formula 7a below with a C10 benzothiazolyl geranyl sulfone compound represented by Chemical Formula 8 below at a molar ratio of 1:2. As such, C20 crocetin dialdehyde represented by Chemical Formula 7a may be obtained by reacting the C5 benzothiazolyl sulfone compound represented by Chemical Formula 1 with C10 octatriene dialdehyde represented by Chemical Formula 6a and then performing acid treatment to remove an acetal protecting group. Furthermore, reacting the C5 benzothiazolyl sulfone compound represented by Chemical Formula 1 with C10 octatriene dialdehyde represented by Chemical Formula 6a may be carried out at a molar ratio of 2:1.

[Chemical Formula 7a]

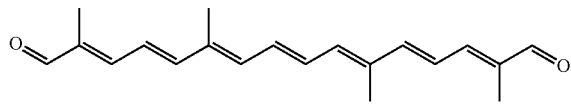

[Chemical Formula 8]

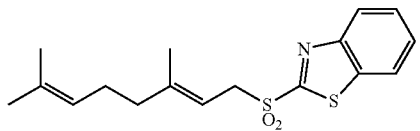

[Chemical Formula 9]

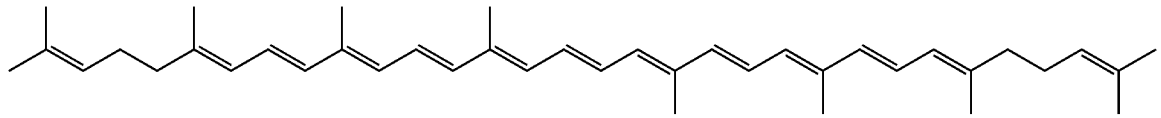

Binding C10 benzothiazolyl geranyl sulfone represented by Chemical Formula 8 with C20 crocetin dialdehyde represented by Chemical Formula 7a may be performed at a low temperature of −78° C. for about 1~2 hr, and Smiles rearrangement and removal of SO₂ and 2-hydroxybenzothiazole may take place simultaneously, thus directly forming a double bond, yielding lycopene represented by Chemical Formula 9. The binding reaction is performed using a base such as NaHMDS, KHMDS, or LiHMDS in the presence of THF solvent, and the use of metal ion such as Na or K is preferable in terms of forming a trans-double bond compared to the use of Li.

The C10 benzothiazolyl geranyl sulfone compound represented by Chemical Formula 8 may be prepared by forming geraniol into methane sulfonate that is then reacted with 2-mercaptobenzothiazole, followed by oxidation of the sulfide into sulfone, based on the method known in literature (Charette, A. B.; Berthelette, C.; St-Martin, D. *Tetrahedron Lett.* 2001, 42, 5149-5153).

According to the present invention, olefination (Julia-Kocienski) between a benzothiazolyl sulfone compound and polyene dialdehyde can be efficiently carried out at a low temperature of −78° C. for about 1~2 hr, compared to a Wittig reaction using a Wittig salt at a high temperature through microwave application, and also it is easy to form the E-double bond configuration. Also, the sulfone compound necessary for the reaction can be easily prepared and has high stability and high crystallinity, thus facilitating the separation and purification thereof.

According to the present invention, polyene dialdehyde compounds are apo-carotene compounds produced in the course of oxidizing a carotene compound, and possess biochemical activities and are useful for the synthesis of natural carotene compounds. Moreover, when polyene dialdehyde is introduced with a proper functional group at both terminals thereof, it can be utilized in electrical and electronic materials such as organic molecular wires, etc.

DESCRIPTION OF SPECIFIC EMBODIMENTS

A better understanding of the present invention may be obtained via the following examples that are set forth to illustrate, but are not to be construed as limiting the present invention, as will be apparent to those skilled in the art.

Example 1

Synthesis of 2-Methyl-2-vinyloxirane (Chemical Formula 2)

In a cold bath (0~4° C.), isoprene (25 mL, 17.03 g, 0.250 mol) was added with DMSO (4 mL) and H₂O (80 mL) and stirred, and the resulting stirred solution was further added with N-bromosuccinimide (35.00 g, 0.197 mol). The reaction mixture was stirred for 2.5 hr, diluted with CH₂Cl₂, dried over anhydrous Na₂SO₄, filtered, and concentrated under reduced pressure, thus obtaining a yellow liquid bromohydrin (37.92 g) as a crude product. The crude product bromohydrin (37.92 g) was added with a 2.7 M NaOH solution (150 mL). The reaction mixture was stirred at room temperature for 1.5 hr. Thereafter, the upper organic layer was separated, yielding a crude product 2-methyl-2-vinyloxirane (15.60 g, 0.185 mol) (yield 94%).

Example 2

Synthesis of (E)-4-(Benzo[d]thiazol-2-ylthio)-2-methylbut-2-en-1-ol (Chemical Formula 3)

Isoprene monoxide (2.64 g, 31.40 mmol) of Chemical Formula 2 was mixed with DMF (30 mL) and stirred, and the resulting stirred solution was added with 2-mercaptobenzothiazole (5.25 g, 31.40 mmol) and CuI (299 mg, 1.57 mmol). The reaction mixture was stirred at room temperature for 21 hr, and added with a 1 M HCl solution to terminate the reaction, and the resulting reaction product was diluted with CH₂Cl₂. The unreacted yellow starting material was removed using a porous glass funnel filter, and the filtrate was washed with a 1 M NaOH solution and H₂O, dried over anhydrous Na₂SO₄, filtered, and concentrated under reduced pressure, thus obtaining a crude product. The crude product was analyzed with ¹H-NMR, yielding a 1,2-addition product (0.68 g, 2.71 mmol, 9% yield, $R_f$=0.31/1:4 EtOAc/hexane), a 1,4-addition product (Z-configuration, 0.85 g, 3.38 mmol, 11% yield, Rf=0.24/1:4 EtOAc/hexane), and a 1,4-addition product (E-configuration, Chemical Formula 3, 3.40 g, 13.53 mmol, 43% yield, $R_f$=0.15/1:4 EtOAc/hexane) at a ratio of 1:1.25:5 from the sulfide.

Data for Chemical Formula 3:
¹H NMR δ 1.76 (br s, 1H), 1.79 (s, 3H), 4.04 (d, J=8.0 Hz, 2H), 4.05 (s, 2H), 5.72 (tq, $J_t$=8.0, $J_q$=1.6 Hz, 1H), 7.29 (t, J=8.0 Hz, 1H), 7.41 (t, J=8.0 Hz, 1H), 7.50 (d, J=8.0 Hz, 1H), 7.87 (d, J=8.0 Hz, 1H) ppm; ¹³C NMR δ 13.6, 31.0, 67.2, 117.7, 120.8, 121.2, 124.1, 125.9, 135.0, 140.8, 152.9, 166.8 ppm; IR (KBr) 3338, 2922, 2845, 1669, 1467, 1429, 1326, 1250, 1087, 997, 856, 766, 727, 672 cm⁻¹; HRMS (FAB⁺) calcd for $C_{12}H_{14}NOS_2$ 252.0517. found 252.0515.

Example 3

Synthesis of (E)-4-(Benzo[d]thiazol-2-ylthio)-2-methylbut-2-enal (Chemical Formula 4)

Allylic alcohol (4.92 g, 19.58 mmol, 4:1 E/Z mixture) of Chemical Formula 3 was added with CH₂Cl₂ and stirred, and the resulting stirred solution was added with silica gel (11.0 g) and pyridinium dichromate (11.05 g, 29.37 mmol). The reaction mixture was stirred at room temperature for 21 hr, diluted with $CH_2Cl_2$, filtered with silica, and concentrated under reduced pressure, thus obtaining a pale brown liquid (yield 72%) as a crude product.

Data for Chemical Formula 4:
$R_f$=0.46 (hexane:EtOAc=4:1); $^1H$ NMR δ 1.86 (s, 3H), 4.21 (d, J=7.6 Hz, 2H), 6.63 (t, J=7.6 Hz, 1H), 7.27 (dd, J=8.0, 7.6 Hz, 1H), 7.39 (dd, J=8.0, 7.6 Hz, 1H), 7.20 (d, J=8.0 Hz), 7.84 (d, J=8.0 Hz), 9.39 (s, 1H) ppm; $^{13}C$ NMR δ 9.3, 30.5, 121.0, 121.5, 124.5, 126.1, 135.4, 141.2, 146.3, 152.8, 164.5, 194.5 ppm; IR (KBr) 1766, 1688, 1464, 1437, 1325, 1246, 1083, 999, 864, 757, 734, 678 $cm^{-1}$; HRMS ($CI^+$) calcd for $C_{12}H_{12}NO_2S_2$ 282.0259. found 282.0257.

Example 4

Synthesis of (E)-2-((3-(5,5-Dimethyl-1,3-dioxan-2-yl)but-2-en-1-yl)thio)benzo[d]thiazole (Chemical Formula 5)

The compound of Chemical Formula 4 (1.98 g, 7.94 mmol) was added with benzene and stirred, and the resulting stirred solution was added with neopentyl glycol (1.24 g, 11.91 mmol) and p-TsOH (76 mg, 0.40 mmol). The reaction mixture was heated for 5 hr using a Dean-Stark column and then cooled to room temperature. The cooled mixture was diluted with diethyl ether, washed with a 1 M NaOH solution and $H_2O$, dried over anhydrous $Na_2SO_4$, filtered, and concentrated under reduced pressure, thus obtaining a crude product. This crude product was purified using silica gel flash column chromatography, yielding a white solid (Chemical Formula 5, 2.34 g, 6.97 mmol) (yield 88%).

Data for Chemical Formula 5:
$R_f$=0.50 (hexane:EtOAc=4:1); $^1H$ NMR δ 0.71 (s, 3H), 1.20 (s, 3H), 1.86 (s, 3H), 3.46 (d, J=10.8 Hz, 2H), 3.63 (d, J=10.8 Hz, 2H), 4.04 (d, J=8.0 Hz, 2H), 4.71 (s, 1H), 5.88 (t, J=8.0 Hz, 1H), 7.26 (dd, J=8.0, 7.6 Hz, 1H), 7.39 (dd, J=8.0, 7.6 Hz, 1H), 7.30 (d, J=8.0 Hz), 7.85 (d, J=8.0 Hz) ppm; $^{13}C$ NMR δ 11.6, 21.8, 23.0, 30.2, 30.6, 77.2, 104.0, 120.9, 121.5, 122.7, 124.2, 126.0, 135.4, 138.1, 153.2, 166.5 ppm; IR (KBr) 2960, 2858, 1729, 1467, 1434, 1385, 1368, 1316, 1275, 1246, 1213, 1102, 1074, 1045, 1008, 984, 935, 865, 767, 731, 678 $cm^{-1}$; HRMS ($CI^+$) calcd for $C_{17}H_{22}NO_2S_2$ 336.1092. found 336.1093.

Example 5

Synthesis of (E)-2-((3-(5,5-Dimethyl-1,3-dioxan-2-yl)but-2-en-1-yl)sulfonyl)benzo[d]thiazole (Chemical Formula 1)

Acetonitrile (50 mL) was mixed with urea-hydrogen peroxide (6.06 g, 64.6 mmol) and phthalic anhydride (4.77 g, 32.2 mmol) and stirred at room temperature for 2.5 hr, thus obtaining a clear solution. In a cold bath (0~4° C.), the sulfide of Chemical Formula 5 (3.60 g, 10.73 mmol, in $CH_2Cl_2$ 10 mL) was added, and the resulting reaction mixture was stirred at room temperature for 17 hr. Most of the solvent was removed under reduced pressure, followed by dilution with $CHCl_3$, after which the undissolved white solid was filtered off. The filtrate was concentrated under reduced pressure, thus obtaining a crude product. This crude product was purified by silica gel flash column chromatography, yielding a white solid (Chemical Formula 1, 3.30 g, 8.99 mmol) (yield 84%).

Data for Chemical Formula 1:
$R_f$=0.20 (hexane:EtOAc=4:1); $^1H$ NMR δ 0.71 (s, 3H), 1.14 (s, 3H), 1.67 (s, 3H), 3.43 (d, J=10.8 Hz, 2H), 3.58 (d, J=10.8 Hz, 2H), 4.30 (d, J=8.0 Hz, 2H), 4.68 (s, 1H), 5.77 (t, J=8.0 Hz, 1H), 7.59 (dd, J=8.0, 7.6 Hz, 1H), 7.64 (dd, J=8.0, 7.6 Hz, 1H), 8.01 (d, J=8.0 Hz), 8.22 (d, J=8.0 Hz) ppm; $^{13}C$ NMR δ 12.1, 21.7, 22.9, 30.1, 54.0, 77.1, 102.8, 112.7, 122.3, 125.4, 127.6, 127.9, 137.0, 144.0, 152.6, 165.5 ppm; IR (KBr) 2971, 2865, 1710, 1674, 1480, 1403, 1326, 1156, 1115, 1030, 985, 912, 852, 730, 689, 641 $cm^{-1}$; HRMS ($CI^+$) calcd for $C_{17}H_{22}NO_4S_2$ 368.0990. found 368.0992.

Example 6

Synthesis of Crocetindial (Chemical Formula 7a)

C5 benzothiazolyl sulfone (3.25 g, 8.85 mmol) of Chemical Formula 1 was dissolved in THF (50 mL) and stirred at −78° C., and the resulting stirred solution was added with a 1 M THF solution of NaHMDS (9.3 mL, 9.3 mmol) and thus turned blackish red. This mixture was stirred for 15 min and added with C10 octatrienedial (727 mg, 4.43 mmol in THF 10 mL) of Chemical Formula 6a. The reaction mixture was stirred at −78° C. for 3 hr and then further stirred at room temperature. This reaction mixture was added with $H_2O$ to terminate the reaction, and the reaction product was extracted with diethyl ether, washed with 1 M NaOH (30 mL×3), dried over anhydrous $Na_2SO_4$, filtered, and concentrated under reduced pressure, thus obtaining an orange solid (3.29 g) as a crude product.

The crude product, the orange solid (3.29 g), was added with THF (30 mL), stirred, and mixed with a 1 M HCl solution (30 mL), giving a red mixture. This mixture was stirred for hr at room temperature in a dark room. The reaction product was diluted with diethyl ether, washed with $H_2O$, dried over anhydrous $Na_2SO_4$, filtered, and concentrated under reduced pressure, thus obtaining a crude product. This was purified by silica gel flash column chromatography, yielding crocetin monoacetal (304 mg, 0.79 mmol) as an orange solid (yield 18%). Subsequently, crocetin dialdehyde (Chemical Formula 7a, 785 mg, 2.65 mmol) was obtained as a red solid (yield 60%). This was further purified by trituration with MeOH to give an analytical sample.

Data for Crocetindial (Chemical Formula 7a):
$R_f$=0.23 (hexane:EtOAc=4:1); $^1H$ NMR δ 1.91 (s, 6H), 2.03 (s, 6H), 6.41-6.52 (m, 2H), 6.68-6.82 (m, 6H), 6.90-7.00 (m, 2H), 9.47 (s, 2H) ppm; $^{13}C$ NMR δ 9.7, 12.8, 123.7, 132.0, 136.7, 137.1, 137.4, 145.4, 148.8, 194.5 ppm; IR (KBr) 3044, 2932, 2839, 2726, 1683, 1624, 1570, 1448, 1418, 1330, 1272, 1198, 982, 845, 747, 698, 645 $cm^{-1}$; UV ($CH_2Cl_2$) λ(ε) 397 (24,944), 422 (51,422), 446 (78,763), 475 (77,058) nm; HRMS (CI %) calcd for $C_{20}H_{25}O_2$ 297.1855. found 297.1852.

Example 7

Synthesis of C30 Tetracosaundecaene Dialdehyde (Chemical Formula 7b)

C5 benzothiazolyl sulfone (0.62 g, 1.70 mmol) of Chemical Formula 1 was dissolved in THF (13 mL) and stirred at −78° C., and the resulting stirred solution was added with a 1 M THF solution of NaHMDS (2.0 mL, 2.0 mmol), thus obtaining a blackish red mixture. This mixture was stirred for 15 min and added with C20 crocetin dial (0.24 g, 0.81 mmol in THF 2 mL) of Chemical Formula 6b (or 7a). The reaction mixture was stirred at −78° C. for 2 hr. This reaction mixture was added with a 10% NH₄Cl solution (5 mL) to terminate the reaction, and the reaction product was extracted with EtOAc, washed with H₂O, dried over anhydrous Na₂SO₄, filtered, and concentrated under reduced pressure, thus obtaining a deep red solid (0.81 g) as a crude product. This was purified by silica gel (deactivated with 2 mL of Et₃N) flash column chromatography, yielding C₃₀ dial (0.24 g, 0.41 mmol) having a neopentyl glycol (diacetal) protecting group as a blackish red solid (yield 50%).

Subsequently, C₃₀ dial (0.93 g, 1.55 mmol) having a neopentyl glycol (diacetal) protecting group was dissolved in THF (30 mL) and stirred, and the resulting stirred solution was added with a 1 M HCl solution (30 mL) and oxalic acid (0.28 g, 3.09 mmol). The reaction mixture was stirred for 3 hr at room temperature in a dark room, diluted with CH₂Cl₂, washed with 1 M HCl, dried over anhydrous Na₂SO₄, filtered, and concentrated under reduced pressure, thus obtaining a crude product. This was purified by silica gel flash column chromatography, yielding C₃₀ polyene dial (0.25 g, 0.57 mmol) of Chemical Formula 7b as a deep violet solid (yield 37%). This was further purified by trituration with MeOH to give an analytical sample.

Data for Chemical Formula 7b:
$R_f$=0.24 (hexane:EtOAc=4:1); ¹H NMR δ 1.91 (s, 6H), 2.01 (s, 6H), 2.03 (s, 6H), 6.32-6.39 (m, 2H), 6.44 (d, J=11.2 Hz, 2H), 6.50 (d, J=14.8 Hz, 2H), 6.65-6.74 (m, 2H), 6.68 (dd, J=15.2, 11.2 Hz, 2H), 6.70 (dd, J=14.8, 10.4 Hz, 2H), 6.75 (d, J=15.2 Hz, 2H), 6.94 (d, J=10.4 Hz, 2H), 9.46 (s, 2H) ppm; ¹³C NMR δ 9.7, 12.8, 12.8, 122.6, 124.9, 131.0, 134.5, 135.3, 136.7, 137.0, 137.6, 140.7, 146.0, 149.3, 194.5 ppm; IR (KBr) 3042, 2926, 2834, 1746, 1678, 1616, 1539, 1457, 1413, 1365, 1331, 1283, 1167, 999, 970, 840, 686 cm⁻¹; UV (CH₂Cl₂) λ(ε) 480 (136,674), 526 (188,406), 550 (167,506) nm; HRMS (FAB⁺) calcd for C₃₀H₃₆O₂ 428.2715. found 428.2704.

Example 8

Synthesis of C40 Dotriacontapentadecaene Dialdehyde (Chemical Formula 7c)

C5 benzothiazolyl sulfone (80 mg, 0.20 mmol) of Chemical Formula 1 was dissolved in THF (8 mL) and stirred at −78° C., and the resulting stirred solution was added with a 1 M THF solution of NaHMDS (0.3 mL, 0.30 mmol). This mixture was stirred for 15 min and added with C₃₀ dial (42 mg, 0.098 mmol in THF 2 mL) of Chemical Formula 6c (or 7b). The reaction mixture was stirred at −78° C. for 2 hr. This reaction mixture was added with a 10% NH₄Cl solution (5 mL) to terminate the reaction, and the reaction product was extracted with EtOAc, washed with H₂O, dried over anhydrous Na₂SO₄, filtered, and concentrated under reduced pressure, thus obtaining a violet solid (70 mg) as a crude product. This was purified by silica gel (deactivated with 2 mL of Et₃N) flash column chromatography, yielding C40 dial (47 mg, 0.064 mmol) having a neopentyl glycol (diacetal) protecting group as a violet solid (yield 65%).

Subsequently, C40 dial (40 mg, 0.050 mmol) having a neopentyl glycol (diacetal) protecting group was dissolved in THF (15 mL) and stirred, and the resulting stirred solution was added with a 1 M HCl solution (15 mL) and oxalic acid (10 mg, 0.11 mmol). The reaction mixture was stirred for 2 hr at room temperature in a dark room, diluted with CH₂Cl₂, washed with 1 M HCl, dried over anhydrous Na₂SO₄, filtered, and concentrated under reduced pressure, thus obtaining a crude product. This was purified by silica gel flash column chromatography, yielding C40 dial (8.4 mg, 0.015 mmol) of Chemical Formula 7c as a violet solid (yield 30%). This was further purified by trituration with MeOH to give an analytical sample.

Data for Chemical Formula 7c:
$R_f$=0.30 (hexane:EtOAc=4:1); ¹H NMR δ 1.91 (s, 6H), 2.00 (s, 6H), 2.01 (s, 6H), 2.03 (s, 6H), 6.28-6.38 (m, 2H), 6.44 (d, J=10.8 Hz, 2H), 6.49 (dd, J=14.8, 11.2 Hz, 2H), 6.51 (d, J=14.8 Hz, 2H), 6.63-6.73 (m, 2H), 6.66 (dd, J=14.8, 10.8 Hz, 2H), 6.68 (d, J=11.2 Hz, 2H), 6.70 (dd, J=14.8, 10.8 Hz, 2H), 6.71 (d, J=14.8 Hz, 2H), 6.75 (d, J=14.8 Hz, 2H), 6.95 (d, J=10.8 Hz, 2H), 9.45 (s, 2H) ppm; IR (KBr) 2927, 2860, 1748, 1677, 1619, 1548, 1455, 1384, 1318, 1256, 1189, 1109, 972, 901, 839, 773, 737, 688 cm⁻¹; UV (CH₂Cl₂) λ(ε) 489 (39,768), 523 (52,517), 556 (47,154) nm; HRMS (FAB⁺) calcd for C₄₀H₄₈O₂ 560.3654. found 560.3646.

Example 9

Synthesis of Lycopene (Chemical Formula 9)

Benzothiazol-2-yl geranyl sulfone (90 mg, 0.27 mmol) of Chemical Formula 8 was dissolved in THF (5 mL) and stirred at −78° C., and the resulting stirred solution was added with a 1 M THF solution of NaHMDS (0.3 mL, 0.30 mmol), thus obtaining an orange mixture. This mixture was stirred for 15 min, and mixed with C20 crocetin dial (40 mg, 0.13 mmol in THF 5 mL) of Chemical Formula 7a. The reaction mixture was stirred at −78° C. for 1.5 hr. This reaction mixture was added with a 10% NH₄Cl solution (5 mL) to terminate the reaction, after which the reaction product was extracted with diethyl ether, dried over anhydrous Na₂SO₄, filtered, and concentrated under reduced pressure, thus obtaining a crude product. This crude product was recrystallized with MeOH/THF, yielding all-(E)-lycopene (104 mg, 0.19 mmol) as a red solid (yield 72%).

Data for Chemical Formula 9:
$R_f$=0.92 (hexane:EtOAc=4:1); ¹H NMR δ 1.61 (s, 6H), 1.68 (s, 6H), 1.82 (s, 6H), 1.96 (s, 12H), 2.11 (br s, 8H), 5.11 (br s, 2H), 5.95 (d, J=10.8 Hz, 2H), 6.18 (d, J=12.1 Hz, 2H), 6.24 (d, J=14.9 Hz, 2H), 6.20-6.30 (m, 2H), 6.35 (d, J=14.8 Hz, 2H), 6.49 (dd, J=14.9, 10.8 Hz, 2H), 6.63 (dd, J=14.8, 12.1 Hz, 2H), 6.55-6.70 (m, 2H) ppm; ¹³C NMR δ 12.8, 12.9, 17.0, 17.7, 25.7, 26.7, 40.2, 123.9, 124.8, 125.1, 125.7, 130.1, 131.5, 131.8, 132.6, 135.4, 136.2, 136.5, 137.3, 139.5 ppm.

What is claimed is:

1. A C5 benzothiazolyl sulfone compound represented by Chemical Formula 1 below;

[Chemical Formula 1]

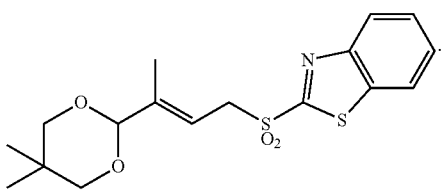

2. A method of preparing the C5 benzothiazolyl sulfone compound of claim 1, comprising:
(a) oxidizing isoprene (C₅H₈), thus synthesizing isoprene monoxide represented by Chemical Formula 2 below;
(b) subjecting the isoprene monoxide to a ring opening reaction using 2-mercaptobenzothiazole, thus synthesizing hydroxyallylic benzothiazolyl sulfide represented by Chemical Formula 3 below;

(c) oxidizing an allylic alcohol group contained in the hydroxyallylic benzothiazolyl sulfide, thus synthesizing an unsaturated aldehyde containing benzothiazolyl sulfide represented by Chemical Formula 4 below;

(d) subjecting the aldehyde to an acetal formation reaction using neopentyl glycol, thus synthesizing an acetal containing benzothiazolyl sulfide represented by Chemical Formula 5 below; and (e) oxidizing benzothiazolyl sulfide of the acetal, thus synthesizing the C5 benzothiazolyl sulfone compound of claim 1;

[Chemical Formula 1]

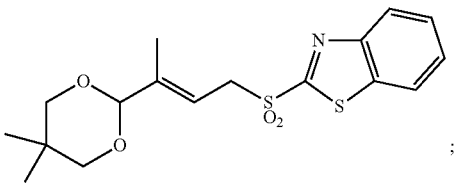

[Chemical Formula 2]

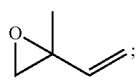

[Chemical Formula 6]

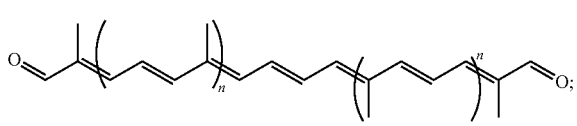

(in Chemical Formula 6, n is 0, 1 or 2)

[Chemical Formula 3]

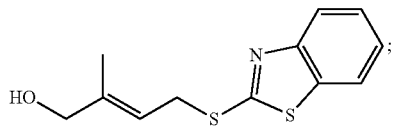

[Chemical Formula 7]

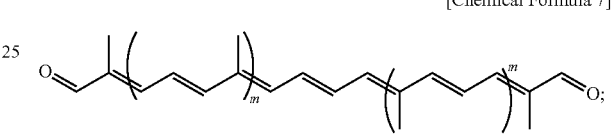

(in Chemical Formula 7, m = n + 1)

[Chemical Formula 4]

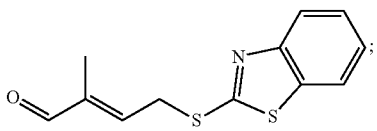

(in Chemical Formula 7, m=n+1).

4. A method of preparing lycopene represented by Chemical Formula 9 below, comprising:
reacting the C5 benzothiazolyl sulfone compound represented by Chemical Formula 1 below with C10 octatriene dialdehyde represented by Chemical Formula 6a below and then performing acid treatment to remove an acetal protecting group, yielding C20 crocetin dialdehyde represented by Chemical Formula 7a below; and
reacting the C20 crocetin dialdehyde represented by Chemical Formula 7a with a C10 benzothiazolyl geranyl sulfone compound represented by Chemical Formula 8 below at a molar ratio of 1:2;

[Chemical Formula 5]

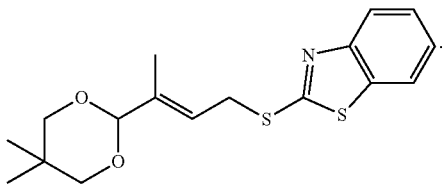

3. A method of preparing polyene dialdehyde represented by Chemical Formula 7 below, comprising: reacting the C5 benzothiazolyl sulfone compound represented by Chemical Formula 1 below with polyene dialdehyde represented by Chemical Formula 6 below at a molar ratio of 2:1, and then performing acid treatment to remove an acetal protecting group;

[Chemical Formula 1]

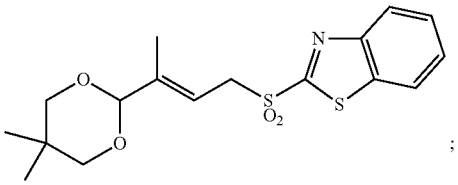

[Chemical Formula 6a]

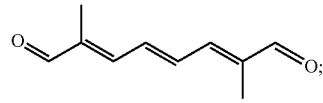

[Chemical Formula 7a]

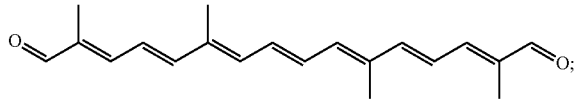

-continued
[Chemical Formula 8]
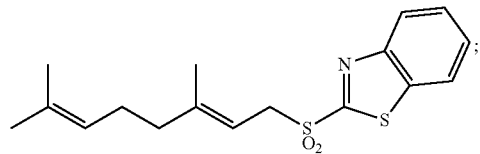
[Chemical Formula 9]
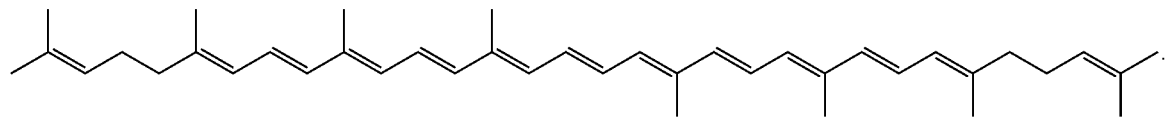
5. The method of claim 4, wherein reacting the C5 benzothiazolyl sulfone compound represented by Chemical Formula 1 with the C10 octatriene dialdehyde represented by Chemical Formula 6a is performed at a molar ratio of 2:1.
* * * * *